US005696166A

United States Patent [19]
Yanni et al.

[11] Patent Number: 5,696,166
[45] Date of Patent: Dec. 9, 1997

[54] COMPOSITIONS CONTAINING HYDROXYEICOSATETRAENOIC ACID DERIVATIVES AND METHODS OF USE IN TREATING DRY EYE DISORDERS

[76] Inventors: John M. Yanni, 2821 Donnybrook, Burleson, Tex. 76028; Daniel A. Gamache, 5610 Hunterwood La.; Steven T. Miller, 5902 Canberra La., both of Arlington, Tex. 76017

[21] Appl. No.: 551,021

[22] Filed: Oct. 31, 1995

[51] Int. Cl.$^6$ .......................... A61K 31/19; A61K 31/215
[52] U.S. Cl. ......................... 514/573; 514/530; 514/912
[58] Field of Search .................................. 514/573, 530, 514/912

[56] References Cited

U.S. PATENT DOCUMENTS

| | | |
|---|---|---|
| 3,991,759 | 11/1976 | Urquhart . |
| 4,131,651 | 12/1978 | Shah et al. . |
| 4,370,325 | 1/1983 | Packman . |
| 4,409,205 | 10/1983 | Shively . |
| 4,744,980 | 5/1988 | Holly . |
| 4,818,537 | 4/1989 | Guo . |
| 4,883,658 | 11/1989 | Holly . |
| 4,906,467 | 3/1990 | Schwartzman et al. . |
| 4,914,088 | 4/1990 | Glonek et al. . |
| 4,966,773 | 10/1990 | Gressel et al. . |
| 5,041,434 | 8/1991 | Lubkin . |
| 5,075,104 | 12/1991 | Gressel et al. . |
| 5,290,572 | 3/1994 | MacKeen . |
| 5,294,607 | 3/1994 | Glonek et al. . |
| 5,358,706 | 10/1994 | Marlin et al. . |
| 5,389,383 | 2/1995 | Huth . |
| 5,403,598 | 4/1995 | Beck et al. . |
| 5,403,841 | 4/1995 | Lang et al. . |

FOREIGN PATENT DOCUMENTS

| | | |
|---|---|---|
| 0 097 059 A2 | 12/1983 | European Pat. Off. . |
| 0 132 089 A1 | 1/1985 | European Pat. Off. . |
| WO 92/04905 | 4/1992 | WIPO . |

OTHER PUBLICATIONS

Graeber et al. "15–Hydroxyeicosatetraenoic Acid Stimulates Migration Of Human Retinal Microvessel Endothelium In Vitro And Neovascularization In Vivo", *Prostaglandins*, vol. 39, No. 6, pp. 665–673 (1990).

Masferrer et al., "12(R)–Hydroxyeicosatetraenoic Acid, An Endogenous Corneal Arachidonate Metabolite, Lowers Intraocular Pressure In Rabbits", *Investigative Ophthalmology And Visual Science*, vol. 31, No. 3, pp. 535–539 (1990).

Wiggins, et al., "12(S)–Hydroxy–5,8,10,14–Eicosatetraenoic Acid Is A More Potent Neutrophil Chemoattractant Than The 12(R) Epimer In The Rat Cornea", *Prostaglandins*, vol. 40, No. 2, pp. 131–141 (1990).

Yanni, et al. Effect of Intravenously Administered Lipoxygenase Metabolites on Rat Trachael Mucous Gel Layer Thickness, *International Archives of Allergy And Applied Immunology*, vol. 90, pp. 307–309 (1989).

Johnson, et al., 15–Hydroxyeicosatetraenoic Acid is a Potent Inflammatory Mediator and Agonist of Canine Tracheal Mucus Secretion, From the Hypersensitivity Diseases Research, Lipids Research, The Upjohn Company, Kalamazoo, Michigan, pp. 917–922 (1984).

Watanabe, et al., Human Corneal and Conjuctival Epithelia Produce a Mucin–like Glycoprotein for the Apical Surface, *Investigative Ophthalmology and Visual Science*, vol. 36, No. 2, pp. 337–344 (1995).

Greiner, et al, Mucus Secretory Vesicles in Conjunctival Epithelial Cells of Wearers of Contact Lenses, *Archives of Ophthalmology*, vol. 98, pp. 1843–1846 (1980).

Dilly, et al., Surface changes in the anaesthetic conjunctiva in man, with special reference to the production of mucus from a non–goblet–cell source, *British Journal of Ophthalmology*, vol. 65, pp. 833–842 (1981).

Shelhamer, et al., The Effects of Arachinoids and Leukotrienes on the Release of Mucus from Human Airways, *Chest Supplement*, 24th Aspen Lung Conference, vol. 81, No. 5, pp. 36S–37S (1982).

Yanni, et al, Effect of Intravenously Administered Lipoxygenase Metabolites on Rat Trachael Mucous Gel Layer Thickness, *International Archives of Allergy And Applied Immunology*, vol. 90, pp. 307–309 (1989).

Marom et al., Human Airway Monohydroxyeicosatetraenoic Acid Generation and Mucus Release, *Journal of Clinical Investigation*, vol. 72, pp. 122–127 (1983).

Graff et al., Activation of Soluble Splenic Cell Guanylate Cyclase by Prostaglandin Endoperoxides and Fatty Acid Hydroperoxides, *Journal of Biological Chemistry*, vol. 253, No. 21, pp. 7662–7676 (1978).

Graff, Preparation of 15–L–Hydroperoxy–5,8,11,13–eicosatetraenoic Acid 915–HPETE), *Methods in Enzymology*, vol. 86, pp. 386–392 (1982).

Corey et al., 12–Hydroxy–5,8,14–(Z)–10–(E)–eicosatetraonoic Acid (12–HETE), *The Logic of Chemical Synthesis*, John Wiley and Sons, sections 12.9 and 12.11 (1989).

Marom et al., Effects of Arachidonic Acid, Monohydroxyeicosatetraenoic Acid and Prostaglandins on the Release of Mucous Glycoproteins from Human Airways In Vitro, *The Journal of Clinical Investigation*, vol. 67, pp. 1695–1702 (1981).

Hamberg et al., Identification of 15–hydroxy–5,8,11,13–eicosatetraenoic acid (15–HETE) as a major metabolite of arachidonic acid in human lung, *Acta Physiol Scand*, vol. 110, pp. 219–221 (1980).

Dohlman, Symposium On The Dry Eye, New Concepts In Ocular Xerosis, *Ophthalmological Societies Of The United Kingdom*, vol. XCI, pp. 105–118 (1971).

Lemp, Tear Substitutes in the Treatment of Dry Eyes, *External Ocular Diseases: Diagnosis And Current Therapy*, Laibson and Trobe (ed.), Little, Brown and Company, Boston, vol. 13, No. 4, pp. 145–153 (1973).

Lemp, Report of the National Eye Institute/Industry Workshop on Clinical Trials in Dry Eyes, *CLAO Journal* vol. 21, No. 4, pp. 221–231 (1995).

*Primary Examiner*—Zohreh Fay
*Attorney, Agent, or Firm*—Michael C. Mayo

[57] ABSTRACT

Compositions containing a HETE derivative and methods of use for treating dry eye are disclosed.

7 Claims, No Drawings

COMPOSITIONS CONTAINING HYDROXYEICOSATETRAENOIC ACID DERIVATIVES AND METHODS OF USE IN TREATING DRY EYE DISORDERS

The present invention is directed to compositions containing certain arachidonic acid metabolites and methods for their use in treating dry eye.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of symptoms outlined above (Lemp, *Report of the Nation Eye Institute/Industry Workshop on Clinical Trials in Dry Eyes*, The CLAO Journal, volume 21, number 4, pages 221-231 (1995))

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et al.), U.S. Pat. No. 4,370, 325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.) and 5,294,607 (Glonek et al.).

United States Patents directed to the use of ocular inserts in the treatment of dry eye include U.S. Pat. No. 3,991,759 (Urquhart). Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290, 572 (MacKeen) discloses the use of finely divided calcium ion compositions to stimulate preocular tear film; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjuctival epithelium of human eyes (Greiner et al., *Mucus Secretory Vesicles in Conjunctival Epithelial Cells of Wearers of Contact Lenses, Archives of Ophthalmology*, volume 98, pages 1843-1846 (1980); and Dilly et al., *Surface Changes in the Anaesthetic Conjunctiva in Man, with Special Reference to the Production of Mucus from a Non-Goblet-Cell Source, British Journal of Ophthalmology*, volume 65, pages 833-842 (1981)). A number of human-derived mucins which reside in the apical and subapical corneal epithelium have been discovered and cloned (Watanabe et al., *Human Corneal and Conjuctival Epithelia Produce a Mucin-Like Glycoprotein for the Apical Surface, Investigative Ophthalmology and Visual Science*, volume 36, number 2, pages 337-344 (1995)). Recently, Watanabe discovered a new mucin which is secreted via the cornea apical and subapical cells as well as the conjunctival epithelium of the human eye (Watanabe et al., *IOVS*, volume 36, number 2, pages 337-344 (1995)). These mucins provide lubrication, and additionally attract and hold moisture and sebacious material for lubrication and the corneal refraction of light.

Mucins are also produced and secreted in other parts of the body including lung airway passages, and more specifically from goblet cells interspersed among tracheal/ bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, *Effect of Intravenously Administered Lipoxygenase Metabolites on Rat Trachael Mucous Gel Layer Thickness, International Archives of Allergy And Applied Immunology*, volume 90, pages 307-309 (1989)). Similarly, Marom has reported the production of mucosal glycoproteins in human lung by HETE derivatives (Marom et al., *Human Airway Monohydroxyeicosatetraenoic Acid Generation and Mucus Release, Journal of Clinical Investigation*, volume 72, pages 122-127

(1983)). Nowhere in the art, however has the use of HETE derivatives been proposed to stimulate mucin production in ocular tissues as a treatment for dry eye.

SUMMARY OF THE INVENTION

The present invention is directed to compositions and methods for the treatment of dry eye and other disorders requiring the wetting of the eye. More specifically, the present invention discloses compositions containing HETE derivatives and methods for treating dry eye type disorders.

Preferred compositions include an effective mount of 15(S)-HETE for the production of mucins. The compositions are administered topically to the eye for the treatment of dry eye.

DETAILED DESCRIPTION OF THE INVENTION

It has now been discovered that certain HETE derivatives stimulate mucin production in human conjuctival epithelium and are therefore believed to be useful in treating dry eye. As used herein, the term "HETE derivative" refers to any hydroxyeicosatetraenoic acid derivative that stimulates mucin production and/or secretion in the conjunctival epithelium and goblet cells following topical ocular application, and are of the following formulas (I), (II) or (III):

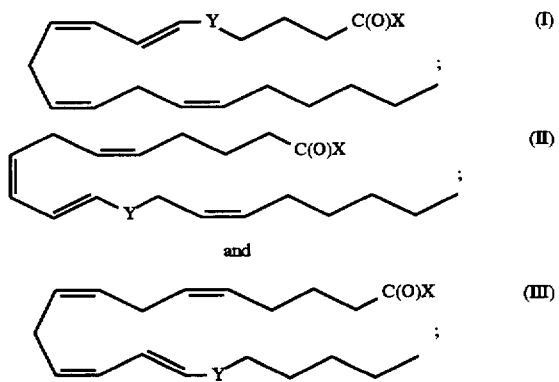

wherein:

X is OR or NHR';

R is H, a cationic pharmaceutically acceptable salt moiety, substituted or unsubstituted alkyl, cycloalkyl, (cycloalkyl) alkyl, aryl, arylalkyl, wherein the substitution is made with a moiety selected from the group consisting of: alkyl, halogen, hydroxy and functionally modified hydroxy;

R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is

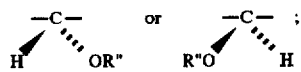

wherein R" is H or C(O)R.

Preferred compounds of the present invention include:

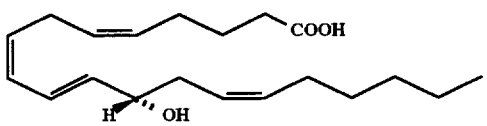

5,8,11,13-Eicosatetraenoic acid, 15-hydroxy-, [S-(E,Z,Z, Z)]-("15(S)-HETE") and

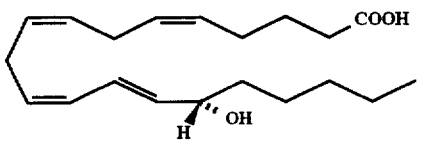

5,8,10,14-Eicosatetraenoic acid, 12-hydroxy-, [S-(E,Z,Z, Z)]-("12(S)-HETE").

15(S)-HETE is a the most preferred HETE derivative of the present invention.

The stereochemistry of the HETE derivatives of the present invention is important. Arachidonic acid occurs naturally as a 20-carbon, 4-double bond molecule. The double bonds are all cis at carbon positions of 5, 8, 11 and 14. Similarly, naturally occurring HETE derivatives resulting from arachidonic acid oxidation, generally contain 4 double bonds between particular carbons and in particular conformations (i.e., cis or trans). As described above, the HETE derivatives of the present invention have double bond conformations of 5,8,11 cis, 13 trans for 15-HETE; 5,8,14 cis, 10 trans for 12-HETE; and, 6 trans, 8,11,14 cis for 5-HETE. As further described above, the hydroxy group can be in the "R" or "S" conformation. Racemic mixtures of HETE derivatives containing R and S hydroxy derivatives at the 5, 12 and 15 positions, respectively, are also contemplated by the present invention.

The HETE derivatives of the present invention are naturally occurring and are derived from arachidonic acid. They are known in the art and have been isolated ex vivo and as well as prepared bio-synthetically and synthetically. HETEs are made endogenously by the action of lipoxygenases or other enzymes and subsequent reductions through the actions of endogenous peroxidases. Several lipoxygenases are known to exist and are named for the carbon position which they oxidize. Such enzymes include 5-lipoxygenase, 12-lipoxygenase and 15-lipoxygenase. Other enzymes such as cytochrome p-450 have been observed to catalyze "R-type" HETE oxidized products. Each lipoxygenase catalyzes the addition of a hydroperoxy group at the respective carbon. After hydroperoxidation, which forms such molecules as 5-hydroperoxyeicosatetraenoic acid ("5-HPETE"), 12-HPETE and 15-HPETE, the arachidonate derivatives are reduced to the resulting alcohol by various peroxidases. The resulting molecules include 5-HETE 12-HETE and 15-HETE.

HETES can be obtained bio-synthetically, by in vitro synthesis. Such methods have involved the use of the respective lipoxygenase, $O_2$, arachidonic acid and a suitable reducing agent (See, Graff et al., *Activation of Soluble Splenic Cell Guanylate Cyclase by Prostaglandin Endoperoxides and Fatty Acid Hydroperoxides, Journal of Biological Chemistry*, volume 253, pages 7662–7676 (1978) and Graff, *Preparation of 15-L-Hydroperoxy-5,8,11,13-eicosatetraenoic acid* (*15-HPETE*), *Methods in Enzymology*, volume 86, pages 386–392 (1982)). HETES may also be synthesized by organic synthetic routes such as described in Corey et al., 12-*Hydroxy*-5,8,14-(Z)-10-(E)-*eicosatetraenoic Acid* (12-*HETE*), *The Logic of Chemical Synthesis*, John Wiley and Sons, sections 12.9 and 12.11 (1989). Finally, HETEs are commercially available from various sources including Sigma Chemical Co. (St. Louis, Mo.) and Cayman Chemical (Ann Arbor, Mich.).

The HETE derivatives of the present invention are intended for administration to a human patient suffering from dry eye. Preferably, the HETE derivatives of the present invention will be administered topically.

The HETE derivatives of the present invention may be contained in various types of pharmaceutical compositions, in accordance with formulation techniques known to those skilled in the art. In general, the HETE derivatives will be formulated in solutions for topical ophthalmic administration. Solutions, suspensions and other dosage forms are particularly preferred for the treatment of dry eye.

The ophthalmic compositions of the present invention will include one or more HETE derivatives in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the HETE derivatives may also be readily incorporated into other types of compositions, such as suspensions, viscous or semi-viscous gels or other types of solid or semi-solid compositions. Suspensions may be preferred for HETE derivatives which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the HETE derivatives from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye and thus eliminate or improve dry eye conditions. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any formulation which is safe, and provides the appropriate delivery for the desired route of administration of an effective amount of at least one HETE derivative of the present invention.

The invention in its broader aspects is not limited to the specific details shown and described above. Departures may be made from such details within the scope of the accompanying claims without departing from the principles of the invention and without sacrificing its advantages.

What is claimed is:

1. A method for the treatment of dry eye comprising administering to a human patient a composition comprising a pharmaceutically acceptable carrier and a pharmaceutically effective amount of one or more HETE derivative according to formulas (I), (II) or (II):

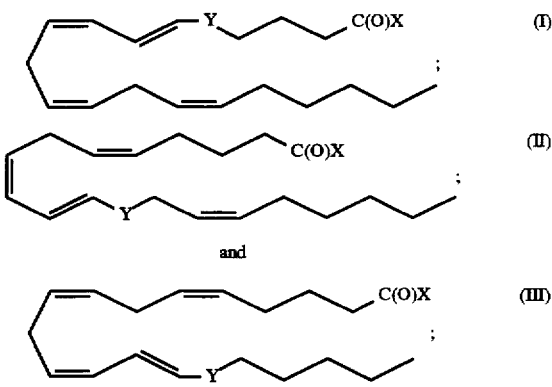

wherein:

X is OR or NHR';

R is H, a cationic pharmaceutically acceptable salt moiety, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy;

R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is

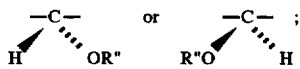

wherein R" is H or C(O)R.

2. The method of claim 1, wherein the HETE derivative is selected from the group consisting of 5(S)-HETE, 5(R)-HETE, 12(S)-HETE, 12(R)-HETE, 15(S)-HETE, 15(R)-HETE and racemates thereof.

3. The method of claim 1, wherein the HETE is 15(S)-HETE.

4. The method of claim 1, wherein the HETE is 12(S)-HETE.

5. The method of claim 1, wherein the composition is a topical ophthalmic formulation.

6. The method of claim 2, wherein the composition is a topical ophthalmic formulation.

7. The method of claim 3, wherein the composition is a topical ophthalmic formulation.

* * * * *

UNITED STATES PATENT AND TRADEMARK OFFICE
CERTIFICATE OF CORRECTION

PATENT NO.    : 5,696,166
DATED         : December 9, 1997
INVENTOR(S)   : Yanni et al.

It is certified that error appears in the above-identified patent and that said Letters Patent is hereby corrected as shown below:

Column 3,
Line 67, "wherein R" is H or C(O)R " should read " wherein R" is H or C(O)R'."

Column 4,
Lines 8-9 should read "5,8,10,14-Eicosatetraenoic acid, 12-hydroxy-,
    [S-(E,Z,Z,Z)]- ("12(S)-HETE") and"
Lines 18-19 should read "5,8,11,13-Eicosatetraenoic acid, 15-hydroxy-,
    [S-(E,Z,Z,Z)]- ("15(S)-HETE")."

Column 6,
Line 11, should read ". . .according to formulas (I), (II) or (III):"

Signed and Sealed this

Twenty-first Day of August, 2001

*Attest:*

NICHOLAS P. GODICI
*Attesting Officer*    Acting Director of the United States Patent and Trademark Office